US010760113B2

(12) United States Patent
Parker et al.

(10) Patent No.: US 10,760,113 B2
(45) Date of Patent: Sep. 1, 2020

(54) KINASE ACTIVITY DETECTION METHODS

(71) Applicants: REGENTS OF THE UNIVERSITY OF MINNESOTA, Minneapolis, MN (US); PURDUE RESEARCH FOUNDATION, West Lafayette, IN (US)

(72) Inventors: Laurie L. Parker, Minneapolis, MN (US); Tzu-Yi Yang, West Lafayette, IN (US); Vincent Davisson, West Lafayette, IN (US)

(73) Assignees: REGENTS OF THE UNIVERSITY OF MINNESOTA, Minneapolis, MN (US); PURDUE RESEARCH FOUNDATION, West Lafayette, IN (US)

(*) Notice: Subject to any disclaimer, the term of this patent is extended or adjusted under 35 U.S.C. 154(b) by 83 days.

(21) Appl. No.: 15/207,379

(22) Filed: Jul. 11, 2016

(65) Prior Publication Data
US 2017/0009273 A1 Jan. 12, 2017

Related U.S. Application Data

(60) Provisional application No. 62/255,198, filed on Nov. 13, 2015, provisional application No. 62/191,027, filed on Jul. 10, 2015.

(51) Int. Cl.
*C12Q 1/48* (2006.01)
(52) U.S. Cl.
CPC ......... *C12Q 1/485* (2013.01); *G01N 2458/15* (2013.01)
(58) Field of Classification Search
CPC ....... C12N 9/12; C12Q 1/485; G01N 2458/15
See application file for complete search history.

(56) References Cited

U.S. PATENT DOCUMENTS

| | | | |
|---|---|---|---|
| 4,612,302 A | 9/1986 | Szabo et al. | |
| 4,684,620 A | 8/1987 | Hruby et al. | |
| 4,853,371 A | 8/1989 | Coy et al. | |
| 2008/0138836 A1 | 6/2008 | Michaud et al. | |
| 2009/0269773 A1* | 10/2009 | Fantl | G01N 33/5091 435/6.14 |
| 2011/0281289 A1* | 11/2011 | Cutillas | C12Q 1/485 435/15 |
| 2013/0231265 A1 | 9/2013 | Parker et al. | |
| 2014/0072516 A1 | 3/2014 | Parker et al. | |
| 2016/0097084 A1 | 4/2016 | Parker et al. | |
| 2016/0376632 A1 | 12/2016 | Parker et al. | |
| 2017/0342461 A1 | 11/2017 | Parker et al. | |

OTHER PUBLICATIONS

Deng et al., "Encoding substrates with amss tags to resolve stereospecific reactions using Nimzynne", Rapid Commun. Mass Spectrom., 2012, 26, 611-615 (Year: 2012).*

Yeh, et al., "Real time visualization of protein kinase activity in living cells", J Biol Chem 277(13), 11527-11532 (2002).
Zheng, et al., "Ultra-stable organic fluorophores for single-molecule research", Chem Soc Rev 43, 1044-1056 (2014).
Akiba, et al., "Click conjugation of a binuclear terbium(III) complex for real-time detection of tyrosine phosphorylation", Anal Chem 87(7), 3834-3840 (2015).
Bendall, et al., "Single-cell mass cytometry of differential immune and drug responses across a human hematopoietic continuum", Science 332 (6030), 687-696 (2011).
Chozinski, et al., "Twinkle, twinkle little star: photoswitchable fluorophores for super-resolution imaging", FEBS Letters 588, 3603-3612 (2014).
Cui, et al., "Modular, Antibody-free Time-Resolved LRET Kinase Assay Enabled by Quantum Dots and Tb(3+)-sensitizing Peptides", Sci Rep 6, 28971, DOI: 10.1038/srep28971 (2016).
Dai, et al., "Visual snapshots of intracellular kinase activity at the onset of mitosis", Chem Biol 14(11), 1254-1260 (2007).
Ding, et al., "Forster resonance energy transfer-based biosensors for multiparameter ratiometric imaging of Ca2+ dynamics and caspase-3 activity in single cells", Anal Chem 83, 9687-9693 (2011).
Enterina, et al., "Emerging fluorescent protein technologies", Current Opinion in Chemical Biology 27, 10-17 (2015).
Galperin, et al., "Three-chromophore FRET microscopy to analyze multiprotein interactions in living cells", Nat Methods 1, 209-217 (2004).
Gao, et al., "FRET-based activity biosensors to probe compartmentalized signaling", Chembiochem 11(2), 147-151 (2010).
Ghadiali, et al., "Protein kinase-actuated resonance energy transfer in quantum dot-peptide conjugates", ACS Nano 4(8), 4915-4919 (2010).
Grant, et al., "Multiplexed FRET to image multiple signaling events in live cells", Biophysical Journal 95(10), L69-71 (2008).
Hildebrandt, et al., "Luminescent terbium complexes: Superior Forster resonance energy transfer donors for flexible and sensitive multiplexed biosensing", Coordination Chemistry Reviews vol. 273-274, 125-138 (2014).
Horton, et al., "Multiplexing terbium- and europium-based TR-FRET readouts to increase kinase assay capacity", J Biomol Screen 15, 1008-1015 (2010).
Irish, et al., "B-cell signaling networks reveal a negative prognostic human lymphoma cell subset that emerges during tumor progression", Proc Natl Acad Sci 107(29), 12747-12754 (2010).
Irish, et al., "Mapping normal and cancer cell signalling networks: towards single-cell proteomics", Nat Rev Cancer 6(2), 146-155 (2006).
Kienzler, et al., "Novel three-color FRET tool box for advanced protein and DNA analysis", Bioconjug Chem 22, 1852-1863 (2011).
Kim, et al., "Monitoring a coordinated exchange process in a four-component biological interaction system: development of a time-resolved terbium-based one-donor/three-acceptor multicolor FRET system", J Am Chem Soc 132(13), 4685-4692 (2010).

(Continued)

*Primary Examiner* — Ruth A Davis
(74) *Attorney, Agent, or Firm* — Viksnins Harris Padys Malen LLP

(57) ABSTRACT

The invention provides cellular assays for detecting the activity of one or more kinase from multiple conditions simultaneously, by encoding biochemically identical substrates with isotope labels that enable them to be distinguished in pooled samples by mass spectrometry.

14 Claims, No Drawings

(56) References Cited

OTHER PUBLICATIONS

Kubota, et al., "Sensitive multiplexed analysis of kinase activities and activity-based kinase identification", Nat Biotechnol 27 (10), 933-940 (2009).

Kunz, et al., "A high-throughput, multiplexed kinase assay using a benchtop orbitrap mass spectrometer to investigate the effect of kinase inhibitors on kinase signaling pathways", Analytical Chemistry 84(14), 6233-6239 (2012).

Kupcho, et al., "Simultaneous monitoring of discrete binding events using dual-acceptor terbium-based LRET", J Am Chem Soc 129, 13372-13373 (2007).

Kuppers, "Mechanisms of B-cell lymphoma pathogenesis", Nat Rev Cancer 5(4), 251-262 (2005).

Lawrence et al., "Seeing is believing: peptide-based fluorescent sensors of protein tyrosine kinase activity", Chembiochem 8(4), 373-378 (2007).

Lipchik, et al., "A peptide-based biosensor assay to detect intracellular Syk kinase activation and inhibition", Biochemistry 51, 7515-7524 (2012).

Lipchik, et al., "KINATEST-ID: a pipeline to develop phosphorylation-dependent terbium sensitizing kinase assays", J Am Chem Soc 137, 2484-2494 (2015).

Lipchik, et al., "Multicolored, $Tb^{3+}$-Based Antibody-Free Detection of Multiple Tyrosine Kinase Activities", Anal Chem 87(15), 7555-7558 (2015).

Lipchik, et al., "Time-resolved luminescence detection of spleen tyrosine kinase activity through terbium sensitization", Anal Chem 85, 2582-2588 (2013).

Lowe, et al., "Multiplex sensing of protease and kinase enzyme activity via orthogonal coupling of quantum dot-peptide conjugates", ACS Nano 6(1), 851-857 (2012).

Lukovic et al. "Recognition-domain focused chemosensors: versatile and efficient reporters of protein kinase activity", J Am Chem Soc 130(38), 12821-12827 (2008).

Mashinchian, "Impacts of quantum dots in molecular detection and bioimaging of cancer.", BioImpacts 4, 149-166 (2014).

Meredith, et al., "Measurement of kinase activation in single mammalian cells", Nat Biotechnol 18(3), 309-312 (2000).

Ni, et al., "Dynamic visualization of cellular signaling", Advanced in Biochemical Eng Botechnol 119, 79-97 (2010).

Olenych, et al., "The fluorescent protein color palette", Curr Protoc Cell Biol, Chapter 21, Unit 21.5 (2007).

Peyker, et al., "Imaging activation of two Ras isoforms simultaneously in a single cell", Chembiochem 6, 78-85 (2005).

Piljic, et al., "Simultaneous recording of multiple cellular events by FRET", ACS Chem Biol 3(3), 156-160 (2008).

Placzek, et al., "A peptide biosensor for detecting intracellular Abl kinase activity using matrix-assisted laser desorption/ionization time-of-flight mass spectrometry", Anal Biochem 397(1), 73-78 (2010).

Proctor, et al., "Development of a peptidase-resistant substrate for single-cell measurement of protein kinase B activation", Anal Chem 84(16), 7195-7202 (2012).

Resch-Genger, et al., "Quantum dots versus organic dyes as fluorescent labels", Nature Methods 5(9), 763-775 (2008).

Shaner, et al., "Advances in fluorescent protein technology", J Cell Sci 120 (Pt 24), 4247-4260 (2007).

Sharma, et al., "Deep quench: an expanded dynamic range for protein kinase sensors", J Am Chem Soc 129(10), 2742-2743 (2007).

Shults, et al., "A multiplexed homogeneous fluorescence-based assay for protein kinase activity in cell lysates", Nature Methods 2(4), 277-283 (2005).

Soughayer, et al., "Characterization of TAT-mediated transport of detachable kinase substrates", Biochemistry 43(26), 8528-8540 (2004).

Stains, et al. "Interrogating signaling nodes involved in cellular transformations using kinase activity probes", Chem Biol 19(2), 210-217 (2012).

Tang, et al., "Detection of early Abl kinase activation after ionizing radiation by using a peptide biosensor", Chembiochem 13(5), 665-673 (2012).

Terai, et al., "Small-molecule fluorophores and fluorescent probes for bioimaging", Pflugers Arch 465, 347-359 (2013).

Tremblay, et al., "Phosphorylation state-responsive lanthanide peptide conjugates: a luminescence switch based on reversible complex reorganization", Org Lett 8(13), 2723-2726 (2006).

Umezawa, et al., "New trends in near-infrared fluorophores for bioimaging", Analytical Sciences 30, 327-349 (2014).

Vogel, et al., "Improving lanthanide-based resonance energy transfer detection by increasing donor-acceptor distances", J Biomol Screen 11, 439 (2006).

Wang et al., "Multicolor monitoring of dysregulated protein kinases in chronic myelogenous leukemia", ACS Chem Biol 5, 887-895 (2010).

White, et al., "Functional activity of the OCT-1 protein is predictive of long-term outcome in patients with chronic-phase chronic myeloid leukemia treated with imatinib", J Clin Oncol 28(16), 2761-2767 (2010).

Wysocki, et al., "Advances in the chemistry of small molecule fluorescent probes", Current Opinion in chemical Biology 15, 752-759 (2011).

Akiba, et al., "Binuclear terbium(III) complex as a probe for tyrosine phosphorylation", Chemistry 16(17), 5018-5025 (2010).

King, et al., "Monoclonal Antibody Conjugates of Doxorubicin Prepared with Branched Linkers: A Novel Method for Increasing the Potency of Doxorubicin Immunoconjugates", Bioc Chem 10(2), 279-288 (1999).

Robinson, et al., "Optimizing the stability of single-chain proteins by linker length and composition mutagenesis", Proc Natl Acad Sci 95, 5929-5934 (1998).

* cited by examiner

KINASE ACTIVITY DETECTION METHODS

PRIORITY OF INVENTION

This application claims priority from U.S. Provisional Application Ser. No. 62/191,027, filed 10 Jul. 2015 and from U.S. Provisional Application Ser. No. 62/255,198, filed 13 Nov. 2015, the disclosures of which are incorporated herein by reference in their entirety.

GOVERNMENT SUPPORT

This invention was made with government support under CA183671, CA160129 and CA127161 awarded by the National Institutes of Health. The government has certain rights in the invention.

BACKGROUND

Kinase signaling is a major mechanism driving many cancers. While many inhibitors have been developed and are employed in the clinic, resistance due to crosstalk and pathway reprogramming is an emerging problem. High-throughput assays to detect multiple pathway kinases simultaneously could better model these complex relationships and enable drug development to combat this type of resistance.

The discovery that specific molecular targets in cancer can be controlled with kinase inhibitor drugs revolutionized modern chemotherapy and created a new paradigm for drug development and treatment. Based on its blockbuster success, the kinase inhibitor drug imatinib (IM) (also known as Gleevec™), has become the first-line therapy for chronic myeloid leukemia (CML). IM targets the oncogenic kinase Bcr-Abl, the fusion protein resulting from the translocation of chromosomes 9 and 22 (known as the Philadelphia chromosome, the hallmark of CML), and initially induces remission in nearly all CML patients. A significant proportion of these patients (approximately 60-70%) maintain remission for ≥5 years (remarkable for a disease that previously had estimated 5-year survival rates of less than 50%).

Unfortunately, these kinase inhibitor 'magic bullets' are not comprehensively curative. Approximately 10% of CML patients fail to respond at all, even if they are Bcr-Abl positive, and approximately 20-30% of those who initially do respond quickly develop resistance to IM (within 1-5 years). The pharmacodynamic response of a given individual (i.e. the effect of the inhibitor on the kinase in their tumor cells) varies, for example due to pharmacokinetic differences and expression of cellular transporters. Studies have shown that achieving at least 10-fold reduction in the BCR-ABL/ABL1 transcript ratio is the strongest predictor of long-term success on kinase inhibitors in CML (as opposed to the previous benchmark of "major molecular response," MMR, which is a $10^3$-fold reduction in this ratio), however, mRNA levels are not a direct pharmacodynamic effect, they are a result of cell death which is a downstream outcome of the direct action of the drug on its target. Evidence suggests that a >50% reduction in Bcr-Abl substrate phosphorylation (a direct effect) in a patient's tumor cells within the first 28 days of treatment is associated with achieving that 10-fold reduction in transcript ratios. This means that just by looking at the effect of the drug on its target and related pathways, physicians would have the opportunity to change treatment plans within the first month if efficacy was not achieved, but currently, this direct pharmacodynamic response is not measured in the clinic.

The complexity of the signaling pathways can also be a confounding factor. Since other kinases (such as the JAK2 and Src-family pathways) can also contribute to CML, some drugs may hit one target but miss other crucial drivers of disease. This is important in CML resistance and relapse, but especially a problem with other leukemias, e.g. Ph+ acute myelogenous (AML) and acute lymphocytic (ALL) leukemias, which frequently do not respond to kinase inhibitors for reasons that are not well understood. In chronic lymphocytic leukemia (CLL), the mobilized, circulating tumor cells tend to be drug sensitive while those sequestered in lymphatic tissue are resistant (possibly due to competing survival signals maintained by the microenvironment). As a result, despite being a relatively low ($9^{th}$) in the list of cancer incidence in the US and despite the success of IM, leukemias still represent the $6^{th}$ most deadly class of cancer. Clearly there is still a need for better management of these diseases.

The heterogeneity of cancer signaling (including differences between individuals and within a given individual's disease) is a major challenge to drug discovery and dosage for kinase inhibitors. Primary cancers are vastly heterogeneous, with an array of genetic and proteomic characteristics. Therefore, it is not surprising that many kinase inhibitor drugs fail clinical trials; if every patient has a novel tumor population phenotype (that furthermore differs from the model systems used to develop the drug), predicting response de novo is next to impossible, and success in some patients is diluted in statistical analysis by lack of response in others. "Personalized medicine" has emerged to address this, however, applications of this concept in the clinic have been limited to the genetic level. Many critical features of kinase signaling are regulated at the post-translational level (e.g. modifications of kinase or substrate, subcellular scaffolding, and localized sequestration), for which genetic techniques are not informative. In addition, drug discovery does not usually incorporate pre-clinical examination of heterogeneity at the post-translational level. Though there are some methods that can approach this (such as immunostaining and flow cytometry profiling of patient tumor cells), they are generally low-throughput and unsatisfactory for highly multiplexed applications.

Kinase inhibitors represent $12 billion of today's oncology drug market (~19% of the total cancer therapeutics market) and their share is projected to keep growing (reaching upwards of $17 billion by 2017). Imatinib will soon be off-patent and will become widely available as a generic (at approximately 10-fold lower cost), so it will likely continue to be the primary first-line treatment for CML, however, competitor next-generation inhibitors are now being pushed to replace imatinib. These more expensive inhibitors may or may not be better for a given patient, and doctors will need pharmacodynamic information to make the right decisions, avoiding excessive costliness while making sure a drug is working for a patient. Accordingly, methods to monitor, manage and optimize kinase inhibitor choice will be crucial to controlling costs and improving patient outcomes. The future of inhibitor treatment management, as well as pre-clinical and clinical inhibitor development, will require expansion of the toolbox to build integrated pictures of signaling dynamics in cultured and primary cells.

Since it is routinely used for metabolite analysis, many clinical labs have targeted MS instrumentation available. Cell-based kinase profiling technology could transform inhibitor treatment at all stages: drug discovery, pre-clinical and clinical development, and patient care. It could aid target validation by providing on- and off-target information. It could improve the analysis of meaningful outcomes in pre-clinical and clinical trials, and it could enable specialization of treatment for individual cancer patients, allowing 'real-time' dose adjustment to reach a given patient's optimal therapeutic window for kinase inhibition.

Currently, the most informative diagnostic markers (BCR-ABL/ABL1 transcript ratios) are first assessed at three months after initiating imatinib or other kinase inhibitor treatment. The monetary cost of three months of unsuccessful imatinib treatment approaches $20,000 per patient, with approximately 4800 new cases of CML per year and 3-month failure rate of ~10%. This translates to nearly $100 million in costs, skyrocketing even more when the rate of relapse within 1-5 years is taken into account. More importantly, this wasted time represents lost opportunities to improve a patient's treatment and potentially position them for long-term success. Strategies that address this gap in the standard of care for CML could transform kinase inhibitor treatment, and serve as a model system for introducing pharmacodynamics into personalized medicine in other cancers. Based on the current evidence, these strategies will require cell-based measurements of kinase activity in a patient's own tumor cells. Furthermore, focusing on inhibitor combinations for more than one kinase at a time will facilitating characterization of key on- and off-target inhibitory effects of multiple compounds in the same cell, revealing early stages of resistance, and enabling timely intervention.

Multiplexed kinase activity detection has remained a challenge in the field, with only a few examples of successful implementation. Existing examples of this strategy typically use dual antibody labelling, with one antibody tagged with a small molecule fluorophore for emission and the other labelled with a chelated lanthanide for sensitization. Alternatively, existing examples tag the substrate with a fluorophore (either small molecule or protein) and use a phosphospecific antibody labelled with a chelated lanthanide for sensitization. In either case, highly specific antibodies are required (but may not be available for the desired analytes) to enable multiplexing.

Genetically-encoded FRET-based sensor proteins are the current state-of-the-art for fluorescence detection of phosphorylation dynamics in live cells, and have led to significant advances in analyzing intracellular kinase activity (Gao, X.; Zhang, J., *Chembiochem* 2010, 11 (2), 147-51; and Ni, Q.; Zhang, J., *Advances in biochemical engineering/biotechnology* 2010, 119, 79-97). However, because these sensors require expression by the cell, and there are only a certain number of genetically-encodable FRET pairs currently available, it is not practical to analyze more than 1-2 kinase targets at a time using this technique (Grant, D. M., et al., *Biophysical journal* 2008, 95 (10), L69-71; and Piljic, A.; Schultz, C., *ACS Chem Biol* 2008, 3 (3), 156-60). Synthetic and FRET-based peptide kinase substrates (Lawrence, D. S.; Wang, Q., *Chembiochem* 2007, 8 (4), 373-8; Sharma, V., et al., *J Am Chem Soc* 2007, 129 (10), 2742-3; Wang, Q., et al., *ACS Chem Biol* 2010, 5 (9), 887-95; Shults, M. D., et al., *Nature Methods* 2005, 2 (4), 277-283; Lukovic, E., et al., *J Am Chem Soc* 2008, 130 (38), 12821-7; Stains, C. I., et al., *Chem Biol* 2012, 19 (2), 210-7; Ghadiali, J. E, et al., *ACS nano* 2010, 4 (8), 4915-9; and Lowe, S. B, et al., *ACS nano* 2012, 6 (1), 851-7) could potentially be more multiplex-compatible (based on the options for synthetic fluorophores), however, while they have been successful in cell lysates, they have had limited application to intact cells, and may be limited by their intrinsic signal to noise (which is usually on the order of 3-5-fold signal enhancement upon phosphorylation) (Yeh, R. H, et al., *J Biol Chem* 2002, 277 (13), 11527-32; and Dai, Z, et al., Chem Biol 2007, 14 (11), 1254-60).

Proteomic assays (e.g. KAYAK, Kubota, K, et al., *Nat Biotechnol* 2009, 27 (10), 933-40; and Kunz, R. C, et al., *Analytical Chemistry* 2012, 84 (14), 6233-6239) are excellent for in vitro multiplexing, but since they are performed with cell lysates, cellular context and any associated regulation are lost. Also, concentrations of drug and enzyme interacting inside the cell are not the same as the concentrations of these components in lysate, thus, the relative "dose" of inhibitor experienced by the enzyme is very different post-lysis. Furthermore, lysate-based assays don't take into account drug uptake differences (through e.g. the OCT-1 transporter (White, D. L, et al., *J Clin Oncol* 2010) or efflux (through multidrug resistance pumps). All of these can confound the interpretation of drug pharmacology when attempting to assess the degree of kinase inhibition in a patient's tumor cells. Synthetic substrates can be tagged for cell uptake using cell penetrating peptides and other cell membrane permeable moieties, and it has been shown that they can be phosphorylated in a kinase-specific manner (Placzek, E. A, et al., *Anal Biochem* 2010, 397 (1), 73-8; Lipchik, A. M, et al., *Biochemistry* 2012, 51 (38), 7515-7524; Tang, J, et al., *Chembiochem* 2012, 13 (5), 665-73; Meredith, G. D, et al., *Nat Biotechnol* 2000, 18 (3), 309-12; Soughayer, J. S, et al., *Biochemistry* 2004, 43 (26), 8528-8540; and Proctor, A, et al., *Anal Chem* 2012, 84 (16), 7195-202). However, the previous detection methods employed with these sensors have required extensive handling with unique instrumentation, antibody-based detection, and/or specialized electrophoresis, hampering their widespread application to multiplexed signaling pathways.

Recent work has established multiplexed flow cytometry techniques using tagged antibodies against endogenous kinase substrate phosphorylation sites to map out signaling networks in cell models and primary cells from patients at the single-cell level (Irish, J. M., et al., *Nat Rev Cancer* 2006, 6 (2), 146-55; and Irish, J. M, et al., *Proc Natl Acad Sci USA* 2010, 107 (29), 12747-54). This work has defined many key parameters for how to handle and stimulate primary cells to get realistic signaling behavior. Recent technology development, particularly using inductively-coupled plasma mass spectrometry (ICP-MS) and metal ion-tagged antibodies (Bendall, S. C., et al., *Science* 2011, 332 (6030), 687-96) has expanded the multiplexability of these techniques to >20 sites in a single experiment. While this strategy breaks several boundaries in the field and produces highly biologically relevant data, it is dependent on immunochemistry for antibody recognition of the endogenous sites. Immunochemistry is limited by the need to produce specific antibodies, with varying sensitivity from antibody to antibody, significant background binding unrelated to the epitope of interest, and the requirement for pre-knowledge of meaningful substrate sites. Moreover, any method that detects endogenous phosphoproteins/peptides gives a snapshot of the cell's current steady state, from which transient or time-dependent changes in activity are difficult to dissect.

Accordingly, there is currently a need for new detection strategies that offer sensitive and specific detection of multiple kinase activities that can enhance the depth of information obtained in a screening assay, monitor more than one signal simultaneously and mimic reconstitution of the relevant pathways, without relying on the availability or development of antibodies for detection.

SUMMARY OF THE INVENTION

The invention provides methods for detecting kinase activity that offer sensitive and specific detection of multiple kinase activities, from multiple samples simultaneously in a traceable manner. Such methods can enhance the depth of information obtained in a screening assay since multiple samples can be pooled for analysis while maintaining the ability to identify the activities of each sample individually, monitor more than one signal simultaneously and mimic reconstitution of the relevant pathways, without relying on the availability or development of antibodies for detection. Cell-based assays provide a level of information about drug pharmacology that is not gained through in vitro assays that use extracted cell contents. Monitoring cell-based pharmacodynamics of inhibitors during drug development could save millions of dollars lost on failed clinical trials. During treatment, it could help predict patient outcomes, and even more importantly, provide opportunities for intervention to optimize drug efficacy and/or drug choice.

Accordingly, in one aspect the invention provides a method comprising:

a) contacting a kinase in vitro or in intact cells with an isotope labeled substrate for the kinase; and b) detecting one or more reaction products from the activity of the kinase on the isotope labeled substrate for the kinase wherein the presence or quantity of one or more of the reaction products correlates with the activity of the kinase; and c) performing this process on more than one aliquot of the enzyme or intact cell sample, each with a version of the substrate comprised of amino acids labeled with different isotope-enriched atoms, such that each substrate in each sample is biochemically identical but differentially "traceable" by mass upon pooling and mass spectrometric detection In another embodiment the invention provides a method comprising: contacting a first kinase and a second kinase (either in vitro or in intact cells) with a first peptide and a second peptide, wherein:

i) the first peptide is an isotope labeled substrate for the first kinase; and ii) the second peptide is an isotope labeled substrate for the second kinase;

and detecting one or more reaction products from the activity of the first kinase on the isotope labeled substrate for the first kinase and detecting one or more reaction products from the activity of the second kinase on the isotope labeled substrate for the second kinase, wherein the presence or quantity of one or more of the reaction products from the activity of the first kinase on the isotope labeled substrate for the first kinase correlates with the activity of the first kinase, and wherein the presence or quantity of one or more of the reaction products from the activity of the second kinase on the isotope labeled substrate for the second kinase correlates with the activity of the second kinase; and iii) optionally performing this process on more than one aliquot of the enzyme or intact cell sample, with each substrate for each kinase also designed in subsets with differentially traceable isotope labeling, with each subset used for a different aliquot of the enzyme or intact cell sample (as described in c) above).

It is understood that the methods of the invention can also be used with a plurality of kinases. Therefore, in another embodiment the invention provides a method comprising: contacting a plurality of kinases (either in vitro or in intact cells) with a plurality of peptides, wherein:

i) each peptide is an isotope labeled substrate for one or more of the kinases; and ii) detecting multiple reaction products from the activity of the kinases on the peptides wherein the presence or quantity of the reaction products correlates with the activity of kinases; and iii) optionally performing this process on more than one aliquot of the enzyme or intact cell sample, with each substrate for each kinase also designed in subsets with differentially traceable isotope labeling, with each subset used for a different aliquot of the enzyme or intact cell sample.

Using the methods of the invention it is possible to simultaneously analyze not only different kinase activities (through different substrate sequences for each kinase), but also more than one condition that each set of kinases was subjected to (by tracing each condition via the specific isotope labeling pattern in a different version of each substrate per condition).

The methods of the invention increase the number of kinase assay samples that can be analysed simultaneously in a mass spectrometer, improving the accuracy of quantitative comparisons between assay samples and decreasing total analysis time for examining kinase activity in different assay samples.

Typically, Mass spectrometry is not a "high throughput" method: only one sample can be run at a time, and each sample takes hours to complete. By using the isotope coding strategy as part of the methods of the invention, many samples can be mixed together and run at the same time in that 1-3 hour run.

Additionally, mass spectrometry is also not a method in which quantitative signals from different runs can be reliably compared: the mass spectrometer signal can vary in strength from run to run and day to day, so the most reliable way to quantify signals relative to each other is to have internal comparisons within the same run rather than external comparisons between different runs. The isotope coding strategy of the methods of the invention solves this problem by allowing samples to be mixed and run together in the same run, so that quantitative signals are normalized to each other.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

"Peptide" describes a sequence of 2 to 50 amino acids or peptidyl residues. The sequence may be linear or cyclic. A peptide can be linked to a fluorophore or to a chelating group through the carboxy terminus, the amino terminus, or through any other convenient point of attachment, such as, for example, through the sulfur of a Cysteine.

Isotope Labelled Kinase Substrates

United States Patent Application Publication Number US2013/0231265, which is incorporated herein by reference in its entirety, describes certain specific peptides that are selective substrates for one or more specific kinases. For example, peptides that are specific for Syk, Btk, Src, Jak2, and Abl are described. Additionally, methods for identifying and preparing peptides that are selective for a specific kinase or kinase family are described. Using this information, a peptide that is selective for a specific kinase or kinase family can be identified. Subsequently, the selective peptide can be synthesized, incorporating one or more isotopically labeled amino acids, to provide an isotope labeled kinase substrate that can be utilized in the methods of the invention. The type, number, and position of the isotopically labelled amino acids can be varied to provide multiple final isotope labelled kinase substrates that are optimized for detecting a particular kinase activity from more than one assay carried out under more than one set of conditions in the methods of the invention. Suitable peptides can also be prepared using methods similar to those described in and described U.S. Pat. Nos. 4,612,302; 4,853,371; and 4,684,620, and in published U.S. Patent Application Nos. 2014/0072516 A1 and 2013/0231265 A1. Peptide sequences specifically recited herein are written with the amino terminus on the left and the carboxy terminus on the right.

As used herein, the term, "isotope labeled kinase substrate" includes kinase substrates wherein one or more atom site in the substrate has an isotopic enrichment factor greater than 1. Non-radioactive isotopes are preferred. The term "isotopic enrichment factor" as used herein means the ratio between the isotopic abundance of the atom at a given site and the natural abundance of a specified isotope of that atom. In certain embodiments, a compound has an isotopic enrichment factor of at least 100 at a given atom, at least 1000, at least 3000, at least 4000, at least 4500, at least 5000, at least 5500, at least 6000, at least 6333.3, at least 6466.7, at least 6600, or at least 6633.3.

Kinases

The methods of the invention can be used to assess the activity of any kinase for which an isotope labeled kinase substrate can be prepared. One specific group of kinases is tyrosine kinases, serine kinases and threonine kinases. Another specific group of kinases is the Src-family kinases, Abl-family kinases, and Syk-family kinases. A more specific kinase is a kinase selected from the group consisting of the Src family (Lyn, Src, Hck, Fyn, Fgr, Lck), the JAK family (JAK1, JAK2, JAK3), the Abl family (Abl, Arg), and the Syk family (Zap-70, Syk).

Detection Methods

The methods of the invention enable detection of differentially isotope-labeled kinase substrates using mass spectrometry. Because incorporation of isotope-enriched atoms in the kinase substrate increases the molecular weight of the kinase substrate and its modified derivatives and/or of certain characteristic sequence fragments of the kinase substrate and its modified derivatives, each differentially-labeled substrate and its modified derivatives will have a unique mass and/or pattern of fragment masses detectable by mass spectrometric analysis. As such, sets of kinase substrates and their modified derivatives (e.g. enzymatic reaction products) that are biochemically identical (i.e. have the same amino acid sequence and thus the same biochemical interactions with the kinase, such as enzyme specificity and enzyme kinetics for conversion to their reaction products) can be distinguished from each other by their masses and/or the masses of their characteristic fragments. Accordingly, more than one enzymatic reaction can be carried out, under sets of conditions that one desires to compare, using a unique isotope-labeled substrate for the kinase of interest for each condition, and the resulting assay samples (containing unconverted starting material substrate and modified derivative, e.g. enzymatically converted reaction product) for each condition can be pooled and analysed with mass spectrometric detection. The mass spectrometry data can then be processed to extract the substrate/product ratio for each unique isotope-labeled substrate and its modified derivative (e.g. enzymatic conversion product) to determine the extent of modification under each condition.

The invention will now be illustrated by the following non-limiting Examples.

EXAMPLES

Example 1. Development of Isotope-coding Strategy to Enable Sample Pooling

Isotopically labelled amino acids were used to prepare a collection of biochemically-identical biosensors with unique MS signatures. These biosensors were applied to different samples and pools for analysis.

Preliminary versions of the isotope-coded Abl biosensor were synthesized using an N15-labeled Fmoc-alanine monomer, and incorporating 1, 2 or 4 labeled alanines into the peptide. In an initial experiment analyzing a mixture of these peptides co-eluting isotopically-labeled forms for the 0, 1 and 2 label versions for the unphosphorylated form and the 1 and 4 label versions for the phosphorylated form were detected on the SCIEX 5600 LC/MS at all amounts injected from 50 fmol down to 0.5 fmol of each. Extracted ion chromatograms (EICs) for the MS1 parent ions and diagnostic fragment ion EICs of the 0, 1 and 4 label versions show that the peptides can be distinguished by m/z. Details for the retention times and masses observed for precursor (MS1) and fragment (MS2) ions are provided in Table 1.

TABLE 1

Description of LC-MS data obtained for the 50 fmol experiment performed as part of Example 1, as an illustrative example.

| Sequences included in extracted ion chromatogram | Retention time (min) | MS1 m/z peaks observed for the $[M + 2H]^{2+}$ charge state (isotopic envelope) | MS2 m/z peaks extracted as EICs |
|---|---|---|---|
| EAIYAAPFAK, EA*IYAAPFAK, EA*IY A*APFAK | 45.416 | 540.7941, 541.2935, 541.7923, 542.2933, 542.7899, 543.2896, 543.7909 | 4x15N-Ala: y7, b5 1x15N-Ala: b4, b5 |
| EA*IpYAAPFAK, EA*IpYA*A*PFA*K | 43.680 | 580.7771, 581.2764, 581.7757, 582.2765, | 4x15N-Ala: y7, b5 1 or 0x15N-Ala: |

TABLE 1-continued

Description of LC-MS data obtained for the 50 fmol experiment performed as part of Example 1, as an illustrative example.

| Sequences included in extracted ion chromatogram | Retention time (min) | MS1 m/z peaks observed for the [M + 2H]²⁺ charge state (isotopic envelope) | MS2 m/z peaks extracted as EICs |
|---|---|---|---|
| | | 582.7733, 583.2726, 583.7742 | y7, y8 |

A* (bold, underlined) = isotope-labeled Alanine (15N).
pY (underlined) = phosphorylated tyrosine.

These data demonstrate proof-of-concept for the ability to distinguish individual substrates and modified derivatives from a pooled sample through the isotope labelling that encodes their individual identities.

Example 2. Develop MRM Detection of Additional Biosensors for Other Kinases

Biosensors were developed to allow for multiplexed analysis for kinases important to imatinib resistance and CML relapse, e.g. Syk, JAK2 and Src-family kinases.

MRM methods were developed for three biosensors and their phosphorylated counterparts (Table 2.) These methods illustrate that these substrates and their modified derivatives can be detected by mass spectrometry (specifically, targeted multiple reaction monitoring mass spectrometry in this example) through their parent and fragment (product) ion species, and that specific unique fragment (product) ions are observable. This information can be used to design isotope-labeled versions of each of these substrates that would provide differentially traceable substrates with unique masses or fragment masses.

TABLE 2

MRM of JAStide-A, SFAStide-A and SAStide biosensors.

| biosensor | Parent ion mass | Product ion species and mass | RT |
|---|---|---|---|
| JAS | 769.68 (+3) | 979.37 (b9) | 9.9 min |
| pJAS | 796.33 (+3) | 1059.34 (b9) | 9.6 min |
| SFAS | 918.88 (+2) | 750.29 (b7) | 13.7 min |
| pSFAS | 958.87 (+2) | 959.30 (b8) | 12.5 min |
| SAS | 1031.89 (+2) | 895.29 (b8) | 19.2 min |
| pSAS | 714.92 (+3) | 846.22 (b7) | 19.2 min |

Peptides were synthesized via solid phase Fmoc chemistry on 50 µmol resin and purified on an Agilent 1200 Series Prep-HPLC system. Purity of these peptides was confirmed to be approximately 95% on a Thermo LC/MS (Accela/LTQ, Thermo Finnigan) system. Peptides were photo-cleaved before injecting onto an ABSCIEX 5500 Triple quadrupole mass spectrometer for transition optimization. To predict proper fragmentor voltage and collision energy with the Skyline software, we used an equation developed based on empirical observations. Six possible product ions were selected for each biosensor along with predicted fragmentor voltage and collision energy for method development. Subsequently, 12.5 fmol of each peptide was injected onto the 5500 for LC-MRM-MS. Acquired data were analyzed on the Skyline software package from the Maccoss group. Each peptide and its phosphorylated form could be observed through both parent and transition ions, albeit with somewhat low signal to noise. This is likely due to the presence of the biotinylated residue and the highly acidic nature of the sequences (both of which can suppress ionization). The sequences can be redesigned to incorporate a trypsin-cleavable residue N-terminal to the biotin tag, so that the peptides can still be enriched via biotin, but can subsequently be cleaved and left with an additional positively charged residue (C-terminal K) upon trypsin digestion.

Example 3. Apply the Differentially Isotope Labeled Substrates to a Kinase Assay In an illustrative example, differentially isotope-labeled versions of the same kinase substrate peptide, as suggested but not limited to those in Table 1, could be included in a longer polypeptide that also contained a cell penetrating peptide sequence to make a cell-permeable "biosensor" substrate polypeptide. Each of the resulting differentially isotope-labeled biosensor polypeptides could be incubated with cells, such as the human CML cell line K562 (which overexpresses the Bcr-Abl kinase) under different conditions—for example, if four isotope-labeled versions of the biosensor were synthesized, one could be incubated with K562 cells alone, one could be incubated with K562 cells in the presence of a kinase inhibitor for Bcr-Abl kinase, one could be incubated with K562 cells in the presence of the phosphatase inhibitor pervanadate, and one could be incubated with K562 cells in the presence of both pervanadate and a kinase inhibitor for Bcr-Abl kinase. These four biosensor polypeptides would each be phosphorylated or not phosphorylated to different degrees in their respective conditions; after which, the cells could be lysed with a buffer that quenched all kinase activity, the lysates could be pooled, and the pooled lysate processed for analysis by mass spectrometry. Mass spectrometric analysis would enable the degree of enzyme activity under each condition to be determined from the amount of phosphorylated form produced for each of the respective isotope-labeled biosensor polypeptides.

Example 4. Apply the Differentially Isotope-Labeled Substrates to a Patient Cell-Based Assay In another illustrative example, differentially isotope-labeled versions of the same kinase substrate peptide, as suggested but not limited to those in Table 1, the differentially isotope-labeled biosensor polypeptides described in Example 3 above could be incubated with cells, such as different patient-derived cells from a leukemia or other cancer patient, either for multiple different patients, and/or for the same patient under different conditions (such as the treatments described in Example 3 for K562 cells)—for example, if four isotope-labeled versions of the biosensor were synthesized, one could be incubated with cells from Patient A, one could be incubated with cells from Patient B, one could be incubated with cells from Patient C, and one could be incubated with cells from Patient D. These four biosensor polypeptides would each be phosphorylated or not phosphorylated to different degrees in their respective patient samples or conditions; after which, the cells could be lysed with a buffer that quenched all kinase activity, the lysates could be pooled, and the pooled lysate processed for analysis by mass spectrometry. Mass spectrometric analysis would enable the degree of enzyme activity under each condition to be determined from the amount of phosphory-lated form produced for each of the respective isotope-labeled biosensor polypeptides. This information could be used, for example, to interpret how effectively a patient's enzyme was being inhibited if they were undergoing treatment, or to compare the amount of enzyme activity in the cells of different patients.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of detecting the activity of a plurality of kinases, the method comprising:
   i) contacting a plurality of kinases with a first plurality of substrates to provide a first enzymatic reaction sample;
   ii) contacting the plurality of kinases with a second plurality of substrates to a provide a second enzymatic reaction sample, wherein the second plurality of substrates are differentially isotopically labeled versions of the first plurality of substrates;
   iii) pooling the first and second enzymatic reaction samples to provide a pooled enzymatic reaction sample; and
   iv) analyzing the pooled enzymatic reaction sample by mass spectrometry to detect the activity of each kinase in each sample.

2. The method of claim 1 wherein at least one kinase is a Bcr-Abl kinase.

3. The method of claim 1 wherein at least one kinase is a Syk, Jak, or Src kinase.

4. The method of claim 1 wherein the analyzing is carried out at the MS1 level and at the MS2 level.

5. The method of claim 1 wherein the mass spectrometry comprises data-dependent mass spectrometry analysis.

6. The method of claim 1 wherein the mass spectrometry comprises targeted mass spectrometry analysis.

7. The method of claim 1 wherein the mass spectrometry comprises data-independent mass spectrometry analysis.

8. The method of claim 1 wherein contacting the kinases with the first and second plurality of substrates is carried out in the presence of mammalian cells or tissue.

9. The method of claim 8 wherein the mammalian cells or tissue are human cells or tissue.

10. The method of claim 9 wherein the mammalian cells or tissue are derived from human bone marrow or human blood.

11. The method of claim 9 wherein the human has cancer.

12. The method of claim 11 wherein the human is taking one or more kinase inhibiting compounds as a therapy for the cancer.

13. The method of claim 9 wherein the human has leukemia.

14. The method of claim 9 wherein the human has chronic myeloid leukemia.

* * * * *